US00PP08877P

United States Patent [19]

Glicenstein

[11] Patent Number: Plant 8,877

[45] Date of Patent: Aug. 30, 1994

[54] CHRYSANTHEMUM PLANT NAMED RADIANT LYNN

[75] Inventor: Leon Glicenstein, Salinas, Calif.

[73] Assignee: Yoder Brothers, Inc., Barberton, Ohio

[21] Appl. No.: 143,153

[22] Filed: Oct. 29, 1993

[51] Int. Cl.[5] ..... A01H 5/00

[52] U.S. Cl. ..... Plt./76

[58] Field of Search ..... Plt. 76, 79, 80

[56] References Cited

U.S. PATENT DOCUMENTS 4,616,099 10/1986 Sparkes ..... 47/58

OTHER PUBLICATIONS

Broertjes, et al., 1980, "A mutant of a mutant of a ... Irradiation of progressive radiation-induced mutants in a mutation breeding programme with *Chrystanthemum morifolium*", Euphytica, 29:526–530.

Gosling ed., 1979 "The Chrysanthemum Manual–6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

*Primary Examiner*—Howard J. Locker

*Attorney, Agent, or Firm*—Foley & Lardner

[57] ABSTRACT

A Chrysanthemum plant named Radiant Lynn particularly characterized by its flat capitulum form; decorative capitulum type; soft salmon pink ray floret color with dark greyed-purple center of the flower; diameter across face of capitulum of 51 to 60 mm when fully opened; branching pattern is spreading and prolific, with 7 to 9 breaks after pinch when grown outside under natural daylength in fall flowerings, and 6 to 7 breaks after pinch when grown in 10 cm pots for spring flowerings; natural season flower date of August 27 to September 4 when planting rooted cuttings on June 21 to 23 in Salinas, Calif., and of September 27 to 30 when planting rooted cuttings June 11 to 14 in Hightstown, N.J.; flowering response of 45 to 47 days after rooting in no light/no shade programs in spring; plant height of 23 to 25 cm when grown in fall under natural daylength with no growth regulators in New Jersey, 25 to 30 cm when grown in fall under natural daylength in California, and 21 to 23 cm when grown in 10 cm pots in spring with no applications of 2500 ppm B-9 SP; and durable, uniform performance.

1 Drawing Sheet

1

The present invention comprises a new and distinct cultivar of Chrysanthemum, botanically known as *Dendranthema grandiflora*, and referred to by the cultivar name Radiant Lynn.

Radiant Lynn, identified as 8092 (88-264J01), is a product of a mutation induction program. The new cultivar was discovered and selected by Leon Glicenstein on Jul. 8, 1991, in a controlled environment in Salinas, Calif. as one flowering plant within a flowering block established as rooted cuttings from stock plants which had been exposed as unrooted cuttings to an X-ray source of 2000 rads in Fort Myers, Fla. on Mar. 6, 1991. The irradiated parent cultivar was the cultivar identified as Lynn, disclosed in U.S. Plant Pat. No. 8,171, and described as a garden mum with a flat decorative flower; light purple ray floret color with a distinct darker red-purple center of the flower; diameter across face of capitulum of 51 to 60 mm when fully opened; spreading and prolific branching pattern, with 7 to 9 breaks after pinch when grown outside under natural daylength in fall flowerings, and 6 to 8 breaks after pinch when grown in 10 cm ports for spring flowerings; natural season flowering date of August 25 to September 5 when planting rooted cuttings June 21 to 23 in Salinas, Calif., and September 26 to October 10 when planting rooted cuttings June 11 to 18 in Hightstown, N.J.; flowering response of 45 to 50 days after rooting in no light/no shade programs in spring; plant height of 25 to 33 cm when grown in fall under natural daylength with no growth regulators in New Jersey, 20 to 28 cm when grown in fall under natural daylength with no growth regulators in California, and 13 to 20

2 cm when grown in 10 cm pots in spring with 0 to 1 applications of 2500 ppm B-9 SP. The ranges of measurements of Lynn given here are somewhat wider than the measurements given in the plant patent for Lynn. This is based on continuing flowering trials of Lynn after filing the plant patent application for Lynn.

The irradiation program resulting in Radiant Lynn had as its primary objective the expansion of color ranges of the parent cultivar Lynn. The irradiation program comprises irradiating cuttings of the parent cultivar at irradiation levels of 1500, 1750 and 2000 rads. A total of 1140 cuttings harvested from a total of 225 irradiated plants were planted on May 13 and 6, 1991, respectively. Of these, 28 initial selections were made, which selections were then revegetated and reflowered. Three consecutive flowerings resulted in discarding 23 of the original 28 selections on Mar. 19, 1992. Nine reselections were made, which reslections were ultimately discarded on Nov. 10, 1992. The remaining five selections were maintained as PIs (Possible Introductions) and further trialed in Salinas, Calif., Hightstown, N.J. and Leamington, Ontario, Canada, ultimately resulting in the decision to discard one of these codes on May 29, 1992 and to introduce the four remaining selections as Radiant Lynn, Peachy Lynn, Royal Lynn and Soft Lynn. The last three cultivars are disclosed in pending patent applications (08/142,940, 08/143,152, and 08/143,154 respetively).

The first act of asexual reproduction of Radiant Lynn was accomplished when vegetative cuttings were taken from the initial selection in September 1991 in a controlled environment in Salinas, Calif., by technicians working under supervision of Leon Glicenstein.

Horticultural examination of controlled flowerings of successive plantings has shown that the unique combination of characteristics as herein disclosed for Radiant Lynn are firmly fixed and are retained through successive generations of asexual reproduction.

Radiant Lynn has not been observed under all possible environmental conditions. The phenotype may vary significantly with variations in environment such as temperatures, light intensity and daylength without, however, any variation in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif under greenhouse conditions which approximate those generally used in commercial greenhouse practice for small pot spring garden mum production.

The following traits have been repeatedly observed and are determined to be basic characteristics of Radiant Lynn, which, in combination, distinguish this Chrysanthemum as a new and distinct cultivar;

1. Flat capitulum form.
2. Decorative capitulum type.
3. Soft salmon pink ray floret color with dark greyed-purple center of the flower.
4. Diameter across face of capitulum of 51 to 60 mm when fully opened.
5. Branching pattern is spreading and prolific, with 7 to 9 breaks after pinch when grown outside under natural daylength in fall flowerings, and 6 to 7 breaks after pinch when grown in 10 cm pots for spring flowerings.
6. Natural season flower date of August 27 to September 4 when planting rooted cuttings on June 21 to 23 in Salinas, Calif., and of September 27 to 30 when planting rooted cuttings June 11 to 14 in Hightstown, N.J.
7. Flowering response of 45 to 47 days after rooting in no light/no shade programs in spring.
8. Plant height of 23 to 25 cm when grown in fall under natural daylength with no growth regulators in New Jersey, 25 to 30 cm when grown in fall under natural daylength in California, and 21 to 23 cm when grown in 10 cm pots in spring with no applications of 2500 ppm B-9 SP.
9. Durable, uniform performance.

The accompanying photographic drawing is a color photograph of Radiant Lynn grown as a pinched garden mum under natural season outside conditions in Salinas, Calif., with the colors being as nearly true as possible with illustrations of this type. Plants were grown outside and dug and transplanted into 15 cm bulb pans at flowering time for photography purposes.

Of the commercial cultivars known to the inventor, the most similar in comparison to Radiant Lynn is the parent cultivar Lynn. In the above description of Radiant Lynn the ranges of values for Radiant Lynn are much narrower than the ranges of values given for Lynn. This is based on the fact that Lynn was flowered over many years, while Radiant Lynn was flowered over a period of only one and a half years. All traits of Radiant Lynn are similar to those of Lynn, except for the ray floret color. The ray floret color of Radiant Lynn is a soft salmon pink with dark greyed-purple center of the flower, while the ray floret color of Lynn is light purple with a darker purple center of the flower. Radiant Lynn is also readily distinguished from the afore-mentioned sibling cultivars at least in ray floret coloration.

In the following description, color references are made to The Royal Horticultural Society Colour Chart. The color values were determined on plant material grown as a pinched garden mum grown under natural season outside conditions in Salinas, Calif. on Aug. 27, 1993.

Classification:

*Botanical.*—*Dendranthema grandiflora* cv Radiant Lynn.

*Commercial.*—Flat decorative spray pot mum and garden mum.

INFLORESCENCE

A. Capitulum:

*Form.*—Flat.

*Type.*—Decorative.

*Diameter across face.*—51 to 60 mm when fully opened.

B. Corolla of ray florets:

*Color (general tonality from a distance of three meters).*—Soft salmon pink ray floret color with dark greyed-purple center of the flower.

*Color (upper surface).*—Fully mature outer petals between 29D and 36D. Center of the flower strongly overlaid with 186A to 186B.

*Color (under surface).*—Closest to 36B.

*Shape.*—Cross section of young ray florets concave, longitudinal section of outer ray florets convex.

C. Corolla of disc florets:

*Color (mature).*—9A.

*Color (immature).*—144C.

D. Reproductive organs:

*Androecium.*—Present on the disc florets only; very few, no pollen.

*Gynoecium.*—Present on both ray and disc florets.

PLANT

A. General appearance:

*Height.*—23 to 25 cm when grown in fall under natural daylength with no growth regulators in New Jersey, 25 to 30 cm when grown in fall under natural daylength in California, and 21 to 23 cm when grown in 10 cm pots in spring with no applications of 2500 ppm B-9 SP.

*Branching pattern.*—Spreading and prolific, with 7 to 9 breaks after pinch when grown outside under natural daylength in fall flowerings, and 6 to 7 breaks after pinch when grown in 10 cm pots for spring flowerings.

B. Foliage:

*Color (upper surface).*—147A.

*Color (under surface).*—147B.

I claim:

1. A new and distinct Chrysanthemum plant named Radiant Lynn, as described and illustrated.

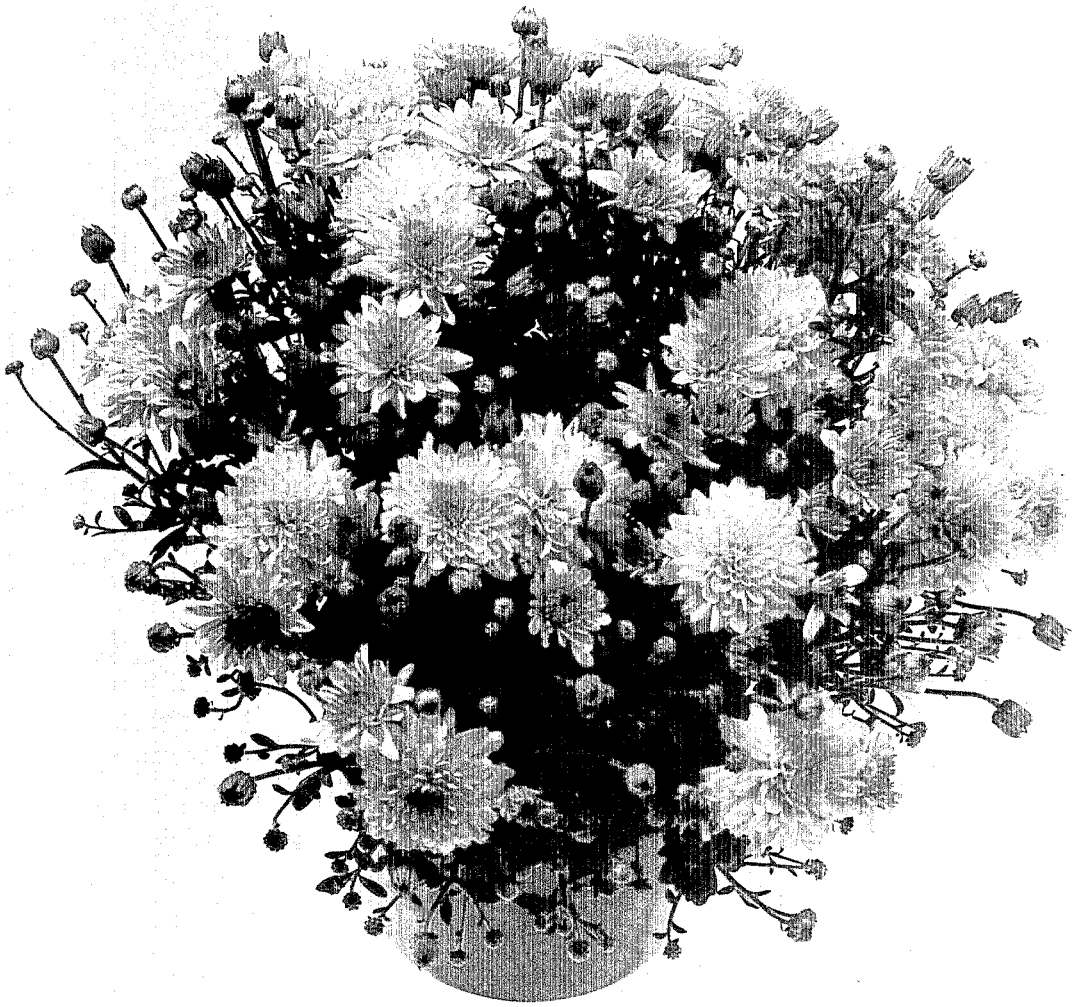

* * * * *